United States Patent
Wachter et al.

(10) Patent No.: US 7,578,667 B2
(45) Date of Patent: Aug. 25, 2009

(54) DENTAL MOLD FLASK

(75) Inventors: Wolfgang Wachter, Schaan (LI); Walter Pokorny, Gais (AT)

(73) Assignee: Ivoclar Vivadent AG, Schaan (LI)

( * ) Notice: Subject to any disclaimer, the term of this patent is extended or adjusted under 35 U.S.C. 154(b) by 190 days.

(21) Appl. No.: 11/899,968

(22) Filed: Sep. 6, 2007

(65) Prior Publication Data
US 2008/0089966 A1 Apr. 17, 2008

(30) Foreign Application Priority Data
Sep. 6, 2006 (DE) .................... 10 2006 041 790

(51) Int. Cl.
*B29C 45/63* (2006.01)
(52) U.S. Cl. .................. 425/175; 425/812; 425/DIG. 11
(58) Field of Classification Search ................. 425/175, 425/812, DIG. 11
See application file for complete search history.

(56) References Cited

U.S. PATENT DOCUMENTS

| 2,030,524 | A | * | 2/1936 | Lambert | 425/175 |
|---|---|---|---|---|---|
| 2,222,531 | A | * | 11/1940 | Dwyer | 425/175 |
| 2,233,295 | A | * | 2/1941 | Miller | 425/175 |
| 2,806,253 | A |   | 9/1957 | Vernon |  |
| 3,277,576 | A | * | 10/1966 | Kraft | 425/175 |
| 3,404,056 | A | * | 10/1968 | Baldwin | 425/388 |
| 3,815,115 | A | * | 6/1974 | Inque | 425/DIG. 11 |
| 5,672,305 | A |   | 9/1997 | Kogure |  |

FOREIGN PATENT DOCUMENTS

| DE | 2331294 | 1/1975 |
|---|---|---|
| DE | 10331863 B3 | 10/2004 |
| GB | 1442041 | 7/1976 |

\* cited by examiner

*Primary Examiner*—Tim Heitbrink
(74) *Attorney, Agent, or Firm*—John C. Thompson; Alan S. Korman; Sandra J. Thompson

(57) ABSTRACT

The invention relates to a dental mold flask (10) for production, in particular for injection molding, of dental molded parts, with at least two mold shells (12) via which a mold cavity (14) can be formed for introduction of polymerizable plastic through a filling channel (16), and with an air release channel (42) for the air that escapes during filling of the mold cavity (14). The air release channel (42) has a filter element (40) whose permeability for air changes automatically, in particular decreases, as soon as it comes into contact with the polymerizable plastic.

12 Claims, 2 Drawing Sheets

DENTAL MOLD FLASK

CROSS-REFERENCE TO RELATED APPLICATIONS

This application claims foreign priority benefits under 35 U.S.C. §119(a)-(d) from German patent application ser. no. 10 2006 041 790.9 filed Sep. 6, 2006.

TECHNICAL FIELD

The invention relates to a dental mold flask for production of dental molded parts, and more particularly for injection molding of dental molded parts, with at least two mold shells via which a mold cavity can be formed for introduction of polymerizable plastic through a filling channel, and with an air release channel for the air that escapes during filling of the mold cavity, which flask serves in particular as an injection mold and, for this purpose, has two mold shells that can be pressed onto one another.

BACKGROUND OF THE INVENTION

Dental mold flasks for the production of dental molded parts have been known for a long time. Such molded parts are often produced as precision-molded parts from a polymerizable plastic which is introduced into the mold cavity via at least one filling channel.

A dental mold flask of this kind is known from U.S. Pat. No. 2,806,253, for example. In such a solution, the flask is fixed with the mold shells in a clamping frame, and the polymerizable material is introduced via a ram that runs within the cooling channel. The polymerizable plastic is cured by being heated.

Numerous improvements to this solution have been proposed over the years. One example of this is to be found in British patent 1,442,041. In this solution, a kind of collar made of an insulating material is provided in the area of the filling channel, and the curing is carried out in a heating bath of boiling water.

It has also already been proposed to arrange an air release channel opposite the filling channel in the flask. The air displaced by the filling process can thus escape, and the degree of filling of the mold cavity can be improved. However, for the heating in boiling water, both the filling channel and also the air release channel then have to be sealed off, and, in an advantageous embodiment, it is also possible, for example, to provide three filling channels and three air release channels, which would then have to be sealed off separately. This is awkward and slows down the production of the prosthesis or of the other molded dental part.

OBJECTS AND SUMMARY OF THE INVENTION

Accordingly, the object of the present invention is to make available a dental mold flask which permits better handling and versatile use.

According to the invention, this object is achieved by providing a dental mold flask for production, in particular for injection molding, of dental molded parts, with at least two mold shells via which a mold cavity can be formed for introduction of polymerizable plastic through a filling channel, and with an air release channel for the air that escapes during filling of the mold cavity, wherein the air release channel has a filter element whose permeability for air changes automatically, in particular decreases, as soon as it comes into contact with the polymerizable plastic.

According to the invention, it is particularly expedient if the air release channel is closed as it were automatically by the filter element in the air release channel as soon as the mold cavity is filled. For this purpose, provision is made for the air release channel to be arranged in a manner known per se opposite the filling channel.

The arrangement should preferably be configured in such a way as to ensure that, when the polymerizable plastic enters the air release channel, no further mold space remains that is not filled with polymerizable plastic. For this purpose, it is also possible for several air release channels to be provided at the appropriate sites, and it is preferable for the air release sub-channels to be routed in such a way that they open into a common air release channel, which again has a filter element.

The filter element is preferably designed as an exchangeable part that has a pore structure and that can be inserted into a receiving recess. The air emerging from the mold cavity is easily able to flow through the filter element, whereas, upon contact with the polymerizable plastic, the pores close. This can either be achieved mechanically, in other words the pore size is chosen such that the surface tension of the still liquid plastic is so great that it is retained in the pores, or it can also be achieved chemically by utilizing the monomers present in the polymerizable plastic in the raw state. Through the contact with the monomers, a change in shape or increase in volume of the filter element can take place, which can be utilized in order to close the pores.

It will be appreciated that the filter element can preferably be designed with open pores. Instead of an open-pore sponge structure, however, it is also possible to use a honeycomb-like body with flow channels through which gaseous media can easily flow. The filter element can also be designed in the manner of a sieve, in which case it is preferably produced as a molded body.

According to the invention, it is particularly expedient if an insulator, which is used for heat insulation, is provided adjacent to the inlet opening. This ensures that the material flowing through the filling channel is not heated too early. The flask can preferably be heated using an inexpensive heater, or, if so required, can also be heated in a water bath with boiling water. In this case too, the filter element then acts as a material barrier in relation to the polymerizable plastic. The heater can also be arranged adjacent to the filter element in order to initiate the curing of the plastic there, that is to say at the most remote site as seen in the direction of filling.

However, the filling channel is preferably provided with an insulator, which ensures that the plastic material introduced there is not immediately heated. This allows the heating to be done over a large surface area and not in a fixed location, so that a filter element that is not especially resistant to temperature can also be used. The insulator then prevents a rapid temperature increase in the filling channel, so that only the mold cavity is hot and, during the curing, a further pressing is effected by the injection molding operation. The quality of the molded part obtained in this way is significantly better, especially when polymethyl methacrylate is used as a main constituent for the polymerizable plastic.

The filter element is preferably connected via the air release channel to a suction device which generates an underpressure. In this way, it is possible to reduce the molding pressure for provision of the plastic by just under 1 bar, for example.

The filter element can be provided at any desired location in the air release channel. However, it is preferably spaced apart slightly, for example by about 1 cm, from the mold cavity in the air release channel. In this way, it is also possible to ensure that the polymerizable plastic cannot be contaminated by the filter element.

According to the invention, it is particularly expedient if the filter element is made of an open-pore material, in particular of an open-pore plastic which, upon contact with monomers contained in the polymerizable plastic, swells and at least partially closes the pores.

According to the invention, it is particularly expedient if the filter element in the starting state, that is to say before contact with the polymerizable plastic, has an open-pore design with a pore size of 1 micrometer to 250 micrometers, preferably between 50 and 150 micrometers.

According to the invention, it is particularly expedient if a suction device is attached to the air release channel, and an underpressure can be established in the air release channel via the suction device, at least before the pressing operation.

According to the invention, it is particularly expedient if the molding pressure of the introduced polymerizable plastic is 1 to 20 bar.

According to the invention, it is particularly expedient if a heat insulator, in particular in two-part form, is arranged adjacent to the inlet opening, and if the inlet opening extends in particular through the heat insulator.

According to the invention, it is particularly expedient if a receiving area for accommodating the polymerizable plastic is made of a heat-insulating material, in particular of a heat-insulating plastic.

According to the invention, it is particularly expedient if the receiving area is composed of two parts, and, in particular, one part of the heat insulator and one part of the receiving area are designed integrally with one another.

According to the invention, it is particularly expedient if the filter element is designed as a molded body.

According to the invention, it is particularly expedient if the filter element can be accommodated in a receiving recess belonging to at least one of the flask halves and forming part of the air release channel, after a corresponding space holder, preferably formed of wax, has been removed.

According to the invention, it is particularly expedient if the filter element, before insertion into the flask, is connected to a positioning aid which is joined to the actual filter element in particular via a predetermined break point and can be removed after insertion of the filter element into the flask.

According to the invention, it is particularly expedient if the air release channel is arranged substantially opposite the air release opening.

According to the invention, it is particularly expedient if an injection device comprises a heating device which interacts with an area of the flask lying opposite the insertion opening.

According to the invention, it is particularly expedient if a heating device for the flask is arranged adjacent to the air release channel and is spaced much further away from the inlet opening than it is from the air release channel.

According to the invention, it is particularly expedient if the heating device overlaps the air release channel and in particular a front part at most, preferably less than a third and in particular only a fifth of the receiving area of the flask.

According to the invention, it is particularly expedient if the air release channel has several, in particular three air release sub-channels that are attached to the receiving area and are routed to the air release channel.

According to the invention, it is particularly expedient if the filter device extends downstream of the air release sub-channels, in particular immediately adjacent to a mouth of the air release sub-channels into the air release channel.

According to the invention, it is particularly expedient if a filter element is provided for each air release sub-channel extending away from the receiving area.

According to the invention, it is particularly expedient if the filter element can be inserted into a receiving recess of at least one of the flask halves and can be removed after completion of the polymerization and separation of the flask halves.

According to the invention, it is particularly expedient if inlet openings are formed lying opposite the air release sub-channels, in particular symmetrical to them.

BRIEF DESCRIPTION OF THE FIGURES

Further advantages, details and features will become evident from the following description of an illustrative embodiment with reference to the drawing, in which.

DETAILED DESCRIPTION

Figure 1:
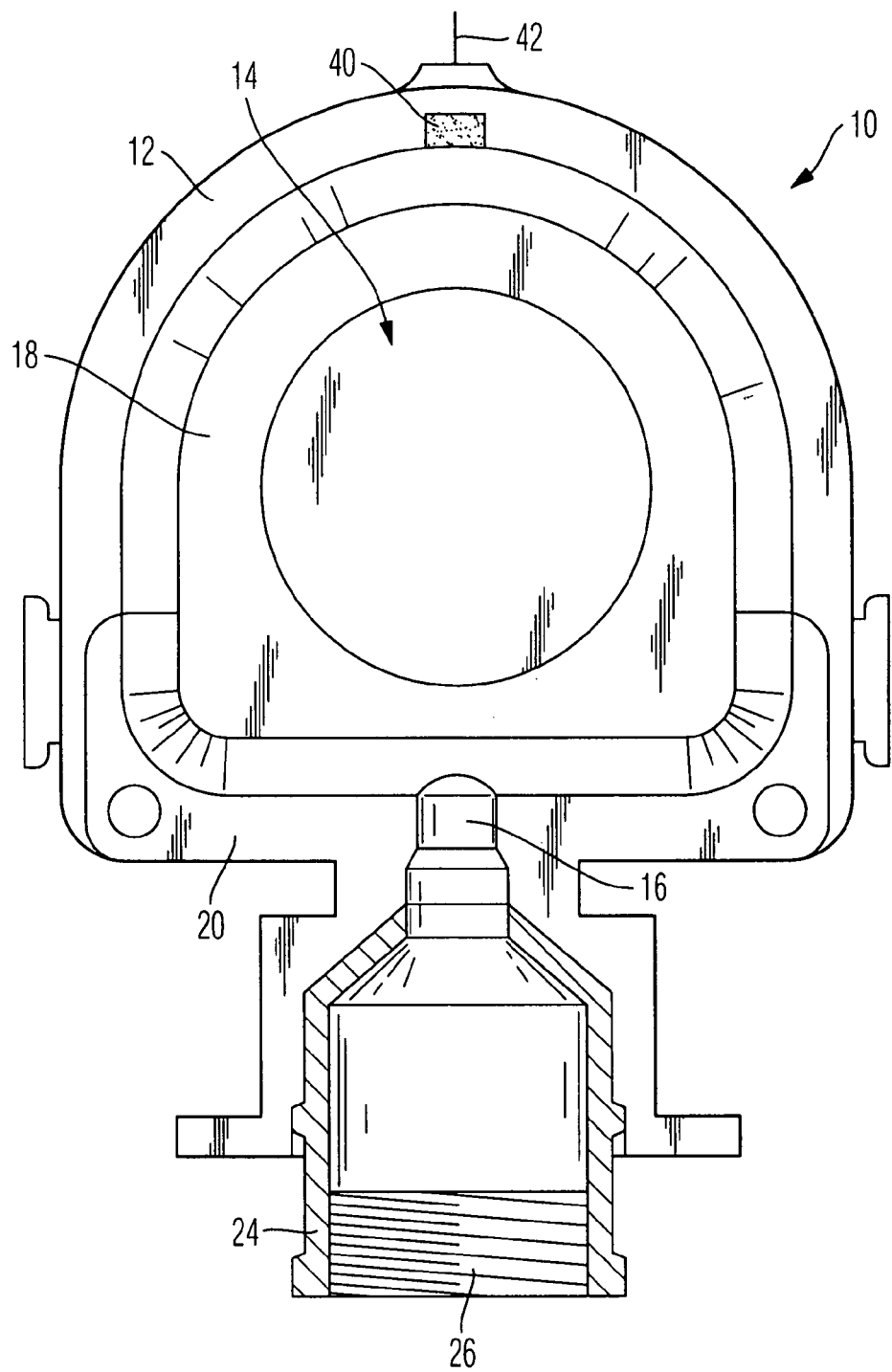
FIG. 1 shows a schematic view of a dental mold flask according to the invention, which includes a filter element.

In FIG. 1, a dental mold flask 10 is shown which is made up of two mold shells that fit one another and of which one mold shell 12 can be seen in FIG. 1. In a manner known per se, the mold shells form a mold cavity 14, which is designed so as to be suitable, for example, for the production of a prosthesis.

The mold cavity 14 can be filled with polymerizable plastic via a filling channel 16. While the mold shells have a housing 18 made of aluminum, the filling channel 16 is surrounded by an insulator 20 which, for example, can be made of a plastic with good heat insulation properties.

The material flowing through the filling channel 16, that is to say the polymerizable plastic material, in this way remains at the filling temperature adjacent to the filling channel, whereas the housing 18 of the dental mold flask 10 is heated by a heating device, and the polymerization takes place rapidly there.

The insulator 20 preferably extends across the entire width of the rear area of the dental mold flask 10, so that curing also does not take place too early there.

The material of the insulator 20 has a low thermal conductivity, but is stable enough to be suitable for receiving a pressure attachment 24 to which the pressing device for introducing the plastic can be connected via an internal thread 26.

According to the invention, the dental mold flask 10 comprises in the front area, that is to say in the area lying remote from the filling channel 16, a filter element 40 which is designed as a porous body and is arranged in a schematically represented air release channel 42.

Figure 2:
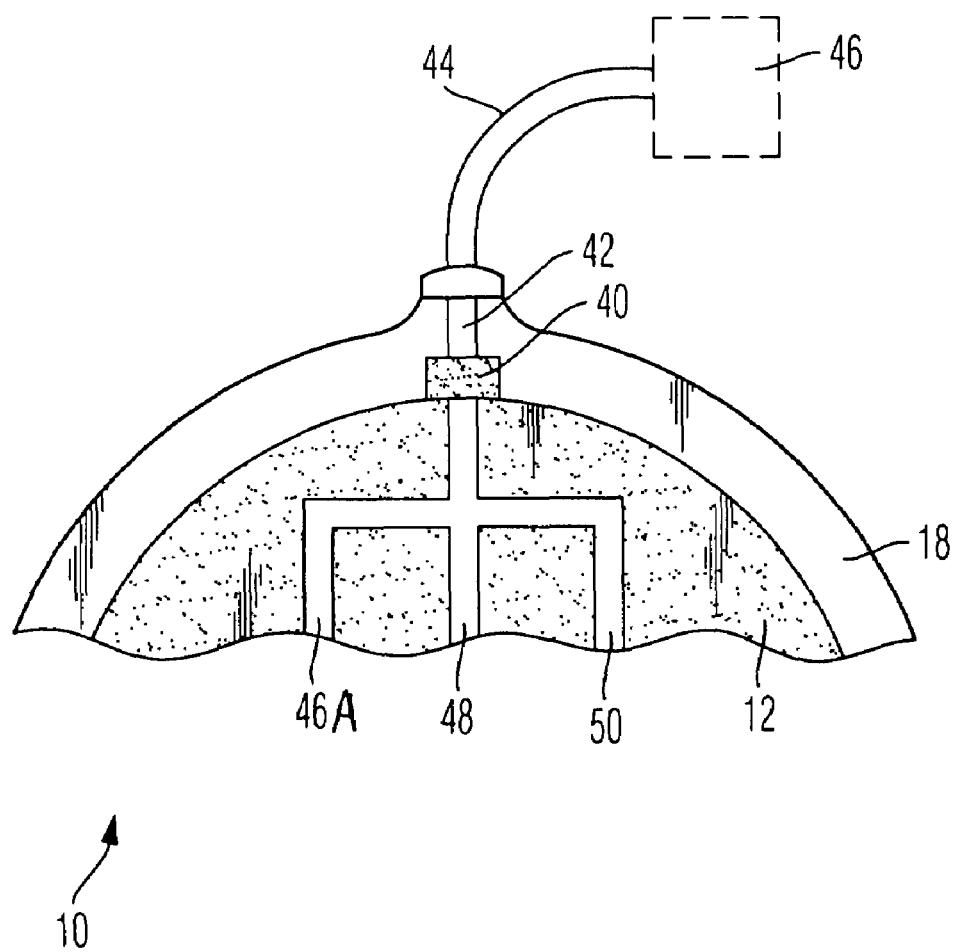
FIG. 2 shows a schematic view of part of the dental mold flask according to FIG. 1, the function of the filter element being made clearer here.

The structure of the filter element and the rest of the arrangement can be better seen in FIG. 2. The filter element 40 is received in the housing 18 of the dental mold flask 10. A suitable receiving recess is formed there for this purpose, for example in the form of a rectangular pocket through which the air release channel 42 is routed. The air release channel 42 is connected via an underpressure line 44 to a suction device 46, in order to make it easier to release air from the mold cavity 14.

The filter element 40 is supported laterally on the housing 18 via the shoulders that are formed there. The shoulders of the housing take up the pressure that is exerted on the filter element 40 when it is acted upon by material from the demolding of the mold shells and completion of the injection molding operation, the filter element is removed from the receiving recess, and the flask is ready to receive a new filter element 40.

The design of the filter element 40 is chosen such that no polymerizable material is pushed through the filter element 40, even at the maximum differential pressure between the underpressure of the suction device 44 and the molding pressure in the filling channel 16. This ensures that the underpressure line 44 and the suction device 46 are also not contaminated by the polymerizable plastic.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A dental mold flask for injection molding, of dental molded parts, with at least two mold shells via which a mold cavity can be formed for introduction of polymerizable plastic through a filling channel, and with an air release channel for the air that escapes during filling of the mold cavity, wherein the air release channel (42) has a filter element (40) whose permeability for air decreases, as soon as it comes into contact with the polymerizable plastic.

2. The dental mold flask as claimed in claim 1, wherein the filter element (40) is made of of an open-pore plastic which, upon contact with monomers contained in the polymerizable plastic, swells and at least partially closes the pores.

3. The dental mold flask as claimed in claim 1, wherein the filter element (40) in the starting state, before contact with the polymerizable plastic, has an open-pore design with a pore size of 1 micrometer to 250 micrometers.

4. The dental mold flask as claimed in claim 1, wherein a suction device (46) is attached to the air release channel (42), and an underpressure can be established in the air release channel (42) via the suction device (46), before the pressing operation.

5. The dental mold flask as claimed in claim 4, wherein the molding pressure of the introduced polymerizable plastic is 1 to 20 bar.

6. The dental mold flask as claimed in claim 1, wherein a heat insulator (20), in particular in two-part form, is arranged adjacent to the inlet opening, and wherein the inlet opening extends through the heat insulator (20).

7. The dental mold flask as claimed in claim 1, wherein a receiving area for accommodating the polymerizable plastic is made of a heat-insulating material.

8. The dental mold flask as claimed in claim 7, wherein the receiving area is made up of two parts, wherein, one part of the heat insulator (20) and one part of the receiving area are designed integral with one another.

9. The dental mold flask as claimed in claim 1, wherein the filter element (40) is designed as a molded body.

10. The dental mold flask as claimed in claim 1, wherein the filter element (40) can be accommodated in a receiving recess belonging to at least one of the mold halves and forming part of the air release channel, after a corresponding space holder has been removed.

11. The dental mold flask as claimed in claim 1, wherein the filter element (40), before insertion into the dental mold flask (10), is connected to a positioning aid which is joined to the actual filter element (40) via a predetermined break point and can be removed after insertion of the filter element (40) into the dental mold flask (10).

12. The dental mold flask as claimed in claim 1, wherein the air release channel is arranged substantially opposite the air release opening.

\* \* \* \* \*

UNITED STATES PATENT AND TRADEMARK OFFICE
CERTIFICATE OF CORRECTION

PATENT NO. : 7,578,667 B2
APPLICATION NO. : 11/899968
DATED : August 25, 2009
INVENTOR(S) : Wolfgang Wachter and Walter Pokorny It is certified that error appears in the above-identified patent and that said Letters Patent is hereby corrected as shown below:

Col. 5; line 34; Claim 2, line 2, the second occurrence of "of" should be deleted.

Col. 6; line 19; Claim 8, line 2, ", wherein," should be rewritten as --wherein--.

Signed and Sealed this

Thirteenth Day of October, 2009

David J. Kappos
*Director of the United States Patent and Trademark Office*